United States Patent [19]

Nelson et al.

[11] Patent Number: 4,512,990

[45] Date of Patent: Apr. 23, 1985

[54] BENZTHIAZINE ANALOGS AS ANTIINFLAMMATORY AGENTS

[75] Inventors: Peter H. Nelson, Los Altos; Howard J. Ringold, Woodside; Stefan H. Unger; Thomas R. Thieme, both of Palo Alto, all of Calif.

[73] Assignee: Syntex (U.S.A.), Inc., Palo Alto, Calif.

[21] Appl. No.: 349,738

[22] Filed: Feb. 18, 1982

[51] Int. Cl.³ .................... C07D 279/16; A61K 31/54
[52] U.S. Cl. ..................................... 514/225; 544/51; 544/52
[58] Field of Search ..................... 544/51, 52; 424/246

[56] References Cited

U.S. PATENT DOCUMENTS

| 2,374,181 | 4/1945 | Dickey et al. | 544/51 |
| 3,117,124 | 1/1964 | Krapcho et al. | 544/51 |
| 3,817,995 | 6/1974 | Bugaut et al. | 544/51 |

Primary Examiner—John M. Ford
Attorney, Agent, or Firm—Ellen J. Buckles; Tom M. Moran; Alan M. Krubiner

[57] ABSTRACT

Compounds of the formula:

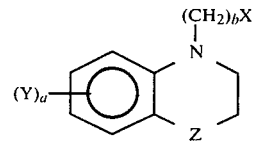

and the pharmaceutically acceptable acid addition salts thereof, wherein:

Z is S;
Y is halo, alkoxy, alkyl, or dialkylamino;
a is 0, 1 or 2;
b is an integer from 2–12 with the proviso that if b is 2 or 3, a cannot be 0, and with the further proviso that if X is OH, b cannot be 2–5 and with the further proviso that if X is —NH$_2$, b cannot be 2–5; and
X is selected from the group consisting of: —OH, OR$^1$, —NH$_2$, —NHR$^1$, NR$^1_2$,

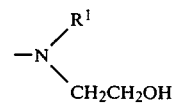

and —NHCONHR$^2$ in which
each R$^1$ is independently alkyl or cycloalkyl or, in —NR$^1_2$, both R$^1$s together are alkylene or form a piperazine ring optionally substituted at the ring N by alkyl or —CH$_2$CH$_2$OH; and
R$^2$ is alkyl, cycloalkyl, or optionally substituted phenyl;

have antiinflammatory properties and are useful in the treatment of conditions characterized by inflammation and swelling.

1 Claim, No Drawings

BENZTHIAZINE ANALOGS AS ANTIINFLAMMATORY AGENTS

BACKGROUND OF THE INVENTION

This invention concerns antiinflammatory agents which are N substituted dihydrobenzothiazines, benzoxazines, and tetrahydroquinolines.

Antiinflammatory activity has been demonstrated for compounds representing a number of structural classes, for example, the corticosteroids, aspirin and related compounds, derivatives of arylacetic and arylpropionic acids and relatives of phenylbutazone. However, no representative of any of these classes is regarded as ideal.

Other compounds which are superficially structurally similar to the compounds of the invention are also known. Those closest in structure to the compounds of the present invention are the compounds disclosed in U.S. Pat. No. 2,374,181, which is directed to certain dye intermediates. Also similar are those in U.S. Pat. No. 2,364,347 which are starting materials for acylamino substituted azo dye precursors.

SUMMARY OF THE INVENTION

The invention herein, in one aspect concerns novel compounds of the formula:

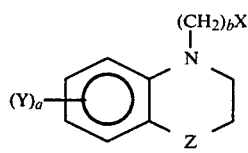

and the pharmaceutically acceptable acid addition salts thereof, wherein:
Z is S;
Y is halo, alkoxy, alkyl, or dialkylamino;
a is 0, 1 or 2;
b is an integer from 2–12 with the proviso that if b is 2 or 3, a cannot be 0, and with the further proviso that if X is OH, b cannot be 2–5; and with the further proviso that if X is $-NH_2$, b cannot be 2–5; and
X is selected from the group consisting of: $-OH$, $OR^1$, $-NH_2$, $-NHR^1$, $NR_2^1$,

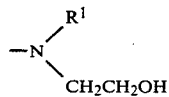

and $-NHCONHR^2$ in which
each $R^1$ is independently alkyl or cycloalkyl or, in $-NR_2^1$, both $R^1$s together are alkylene or form a piperazine ring optionally substituted at the ring N by alkyl or $-CH_2CH_2OH$; and
$R^2$ is alkyl, cycloalkyl, or optionally substituted phenyl.

In another two aspects, the invention relates to pharmaceutical compositions containing a compound of Formula I and to methods of preventing, reducing, or inhibiting inflammation utilizing compounds of formula I or the aforesaid composition. Finally, the invention also relates to a process for the preparation of compounds of formula I, and their salts.

DETAILED DESCRIPTION OF THE INVENTION

Definitions

As used herein:
"Alkyl" means a branched or unbranched saturated hydrocarbon chain containing 1–8 carbon atoms, such as methyl, ethyl, propyl, tert-butyl, n-hexyl, n-heptyl or iso-octyl and the like.

"Alkoxy" means the group $-OR$ wherein R is alkyl as herein defined.

"Cycloalkyl" means saturated carbocyclic rings containing 5–7 carbon atoms.

"Alkylene" means $(CH_2)_n$ wherein n is an integer from 3–8.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Optionally substituted phenyl" means a phenyl moiety, which may or may not be substituted as indicated in the previous paragraph, with 1–3 substituents selected from the group consisting of halo, lower alkyl (1–4C), lower alkoxy (1–4C), hydroxy, and trifluoromethyl.

Certain embodiments of the invention herein contain an amino nitrogen as well as the ring nitrogen—i.e., those cases wherein X and/or Y is chosen so that a primary, secondary, or tertiary amine is in the compound. Thus in all cases, pharmaceutically acceptable acid addition salts may be prepared.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicyclic acid and the like.

The compounds of the invention herein will be named as saturated hydrocarbon backbones with the heterocyclic moieties as substituents. Accordingly, the numbering system for the ring nucleus is shown below:

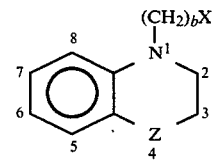

METHODS OF PREPARATION

Compounds of the invention are prepared from the corresponding substituted or unsubstituted 1,2,3,4-tetrahydroquinolines, 2,3-dihydrobenzothiazines, or benzoxazines, by converting them first to the corresponding ω-haloalkanoyl derivatives. This conversion takes place as shown below:

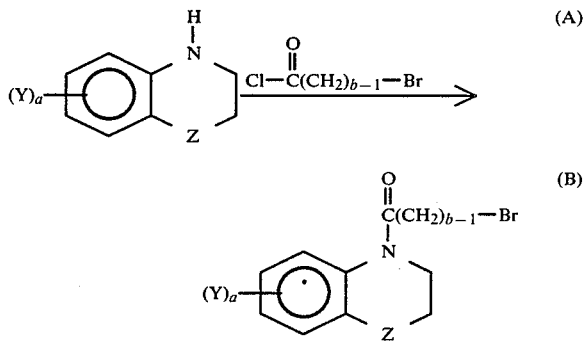

In this conversion, the reagent has been shown as the acyl chloride with an ω-bromo group. However, any suitable halo leaving group can be used in either position, for example, the acyl bromides or ω-chlorides or iodides are also appropriate.

The compounds of formula A are either commercially available, or may easily be prepared by means known in the art.

In carrying out this conversion, the appropriate ω-haloalkanoyl halide is dissolved in an inert aprotic, organic solvent such as ether or dichloromethane, preferably ether. The compound of formula A is dissolved in a similar solvent, along with a molar excess of base optionally in aqueous solution. The base may be any strong inorganic or organic base, such as sodium hydroxide, sodium carbonate, but preferably sodium hydroxide. The reagent mixture is added in approximately equimolar quantity for stoichiometric reaction with the compound of formula A. The resulting mixture is kept at about 30° C. to 150° C., preferably at the reflux temperature of the solvent for about 1 to 8 hours, preferably around 3 hours. The product of formula B is then isolated.

In carrying out the above conversion, and also those set forth below, isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to dryness, and the salts can be further purified by conventional methods.

The compounds of formula B are then converted to the desired compounds of formula 1 by treating with the appropriate reagents:

A. Compounds of formula 1 wherein X is a nitrogen containing substituent other than urea of $NH_2$.

Embodiments of the invention wherein X is $NHR^1$, $NR_2^1$, or $NR^1$—$CH_2CH_2OH$ may be prepared by converting the ω-halo group to the corresponding nitrogen containing residue, and then reducing the carbonyl adjacent to the ring nitrogen. This sequence of reactions is shown below:

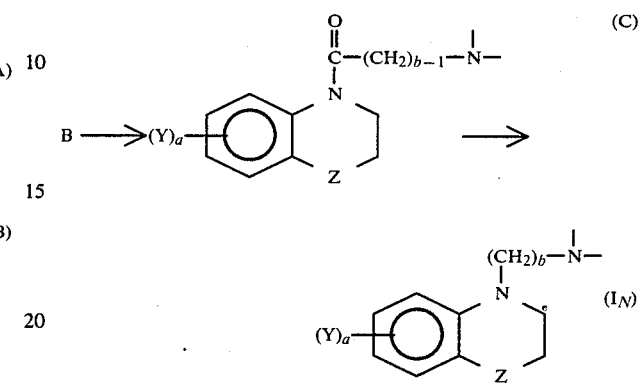

To carry out this conversion, the appropriate primary or secondary amine (to give $X=NHR^1$ or $NR_2^1$, or —$NR^1CH_2CH_2OH$, including of course, the appropriate piperazine derivative, is dissolved in a polarorganic solvent, such as methanol, ethanol or ethylene glycol, preferably ethylene glycol. The compound of formula B is then added to the solution, and the solution heated to 50° to 150°, preferably reflux temperature, for about 15 minutes to 24 hours, preferably about 1 hour. The product of formula C is then isolated, if desired.

The compound of formula C is then added to a stoichiometric excess of an appropriate metal hydride reducing agent in the inert, aprotic, organic solvent, such as ether or tetrahydrofuran. The preferred hydride is lithium aluminum hydride. When the reaction is complete, the compound of formula $I_N$ is isolated conventionally.

B. Embodiments wherein X is $NH_2$.

Compounds of formula 1 wherein X is $NH_2$ are prepared by converting the compound of formula B into the corresponding azido compound, and then reducing with the hydride. This conversion is shown below.

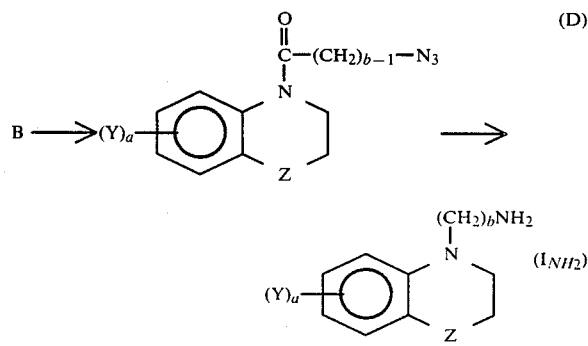

In carrying out this conversion, the compound of formula B is dissolved in an inert, aprotic organic solvent such as dimethylformamide, tetrahydrofuran, or dimethylsulfoxide, preferably dimethylformamide. Also placed in solution are stoichiometric excess of sodium azide, and a suitable alkali metal iodide salt, such as, preferably, sodium iodide. The mixture is heated to about 50° to 150°, preferably about 90° to 100° for several hours, preferably around 2 hours. The product of formula D may then be isolated; it is then refluxed in an ether solution containing a stoichiometric excess of lithium aluminum hydride for about 4–8 hours, preferably around 5 hours until the reaction is complete. The compound of formula $I_{NH_2}$ is then isolated.

C. Compounds of formula 1 wherein X is hydroxy.

Compounds of formula I wherein X is hydroxy ($I_{OH}$) are prepared by heating the compound of formula B with a superoxide, and then reducing the resultant product E to compounds of formula $1_{OH}$. This sequence of reactions is shown:

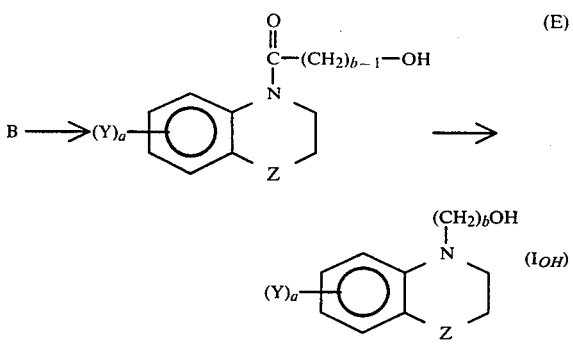

In carrying out this conversion, an approximately equal molar amount of potassium superoxide is added to a solution of the compound of formula B in an aprotic solvent, preferably dimethylsulfoxide. The reaction mixture is kept at about 5° C. to 50° C., preferably room temperature until reaction is complete, usually about 8 hours. The product of formula E is then isolated and dissolved in an inert organic solvent, preferably ether along with a stoichiometric excess of lithium aluminum hydride. The solution is then kept at 30° C. to 100° C., preferably the reflux temperature until reaction is complete. The compound of formula $i_{OH}$ is then isolated.

D. Compounds of the invention wherein X is alkoxy.

When compounds of formula $I_{OR_1}$ are to be prepared, the compound of formula B is dissolved in a suitable alkanol of formula $R_1OH$ and converted to the corresponding compound of formula F which is then converted by treating with a metal hydride to the appropriate compound of formula $I_{OR_1}$ as shown below.

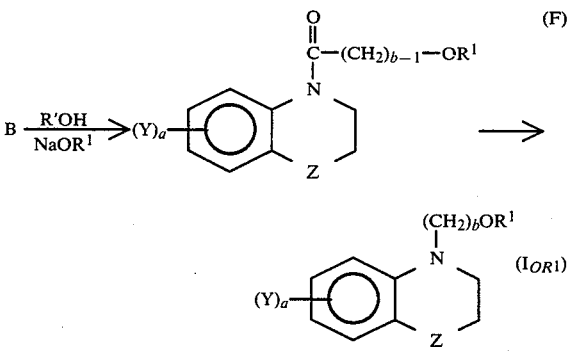

In carrying out this sequence, a sodium alkoxide of formula $NaOR^1$ is added to a solution of the compound of formula B in the corresponding alcohol. The mixture is then kept at 50° to 150°, preferably reflux temperature for 2 to 24 hours, preferably 8 hours. The compound of formula F is then isolated, dissolved in a suitable aprotic solvent, preferably ether and treated with a stoichiometric excess of lithium aluminum hydride. The mixture is refluxed for several hours until the reaction is complete and the compound of formula $I_{OR}$ is then isolated.

E. Embodiments wherein X is a urea residue.

Compounds of formula $I_U$, wherein X is a urea residue are prepared from the corresponding compounds of formula $I_{NH_2}$, by conventional treatment with the appropriate isocyanate, of formula $R^2NCO$. This conversion is well known in the art, and is carried out simply by adding the appropriate isocyanate to a solution of a compound of formula $I_{NH_2}$ in an aprotic solvent and keeping the solution at room temperature until reaction is complete.

All of the compounds of formula I may be converted to their addition salts, by virtue of the presence of the ring nitrogen. In addition, embodiments wherein Y is dialkylamino, and/or X is a nitrogen containing non-urea residue, additional sites of the acid addition are provided.

The compounds of formula I in free base form may be converted to the acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and 50° C. The resulting acid addition salt precipitates spontaneously or may be brought out of solution with a less polar solvent.

The acid addition salts of the compounds of formula I may be decomposed to the corresponding free base by treating with a stoichiometric excess of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Salts of the compounds of formula I may be interchanged by taking advantage of differential solubilities of the salts, volatilities or acidities of the acids, or by treating with the appropriately loaded ion exchange resin. For example, the interchange is effected by the reaction of a salt of the compounds of formula I with a slight stoichiometric excess of an acid of a lower pKa than the acid component of the starting salt. This conversion is carried out at a temperature between about 0° C. and the boiling point of the solvent being used as the medium for the procedure.

Utility and Administration

The compounds of formula I have been shown in standard laboratory tests to inhibit inflammation. Accordingly, the compounds of Formula I or their salts or pharmaceutical compositions containing them, may be used in inhibiting, preventing, or controlling inflammation in mammals.

Administration of the active compounds and salts described herein can be via any of the accepted modes of administration for agents which control inflammation. These methods include oral, parenteral and otherwise systemic or topical.

Depending on the intended mode of administration, the compositions used may be in the form of solid, semisolid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of formula I, either oral or topical administration is preferred depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

For topical administration, these compositions comprises an effective amount of a compound of this class in admixture with a pharmaceutically acceptable non-toxic carrier. A suitable range of composition would be 0.1%–10% active ingredient, and the balance carrier, preferably 1–2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the instant invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other acids such as oleic acid and palmitic acid; and 0 to 20 wt. percent of a penetrant such as dimethyl sulfoxide, dimethylacetamide.

The amount of active compound administered will of course, be dependent on the subject being treated, the severity of the affliction, the manner of administration and the judgement of the prescribing physician. However, an effective dosage is in the range of 1–100 mg/kg/day, preferably about 25 mg/kg/day. For an average 70 kg human, this would amount to 70 mg–7 g per day, or preferably about 1.5 g/day.

Preferred Embodiments

Preferred among the compounds of the invention are those, and their pharmaceutically acceptable salts, wherein a is 0. Preferred among these are those wherein b is an integer between 4 and 8. Especially preferred are those compounds wherein Z is $CH_2$ or S.

Particularly preferred are those compounds and their pharmaceutically acceptable acid addition salts which are selected from the group consisting of:
4-amino-1-(1,2,3,4-tetrahydroquinol-1-yl)butane;
4-amino-1-(2,3-dihydrobenzothiazin-1-yl)butane;
6-amino-1-(1,2,3,4-tetrahydroquinolin-1-yl)hexane;
6-amino-1-(2,3-dihydrobenzothiazin-1-yl)hexane;
6-dimethylamino-1-(1,2,3,4-tetrahydroquinolin-1-yl)hexane;
6-dimethylamino-1-(2,3-dihydrobenzothiazin-1-yl)hexane;
8-amino-1-(1,2,3,4-tetrahydroquinol-1-yl)octane;
8-amino-1-(2,3-dihydrobenzothiazin-1-yl)octane;
8-dimethylamino-1-(1,2,3,4-tetrahydroquinolin-1-yl)octane;
8-dimethylamino-1-(2,3-dihydrobenzothiazin-1-yl)octane.

The following examples serve to illustrate the invention. They should not be construed as narrowing it, or limiting its scope.

PREPARATION 1

Preparation of 1-(4-Bromobutanoyl)-1,2,3,4-tetrahydroquinoline

A. A solution of 4-bromobutyryl chloride (3.4 g) in ether (25 ml) was added to a mixture of 1,2,3,4-tetrahydroquinoline (6.8 g), ether (20 ml) and 10% aqueous sodium hydroxide (34 ml). The mixture was refluxed with stirring for 3 hours then the ethereal solution was washed with dilute hydrochloric acid, dried and evaporated to yield the title compound as an oil.

B. In a manner similar to that set forth in paragraph A, the ω-halo alkanoyl derivatives of 2,3-dihydrobenzothiazine and benzoxazine are prepared.

EXAMPLE 1

Preparation of 6-dimethylamino-1-(1,2,3,4-tetrahydroquinolin-1-yl)hexane 1-(6-bromohexanoyl)-1,2,3,4-tetrahydroquinoline, (4.9 g), prepared in a manner similar to that set forth in Preparation 1, was refluxed, using a dry ice condenser, in a saturated solution of dimethylamine in ethylene glycol (46 ml). After 45 minutes the solution was cooled and added to dilute aqueous potassium hydroxide. The resultant solution was extracted with ether, and the extract was washed, dried and evaporated to yield as an oil 1-(6-dimethylaminohexanoyl)-1,2,3,4-tetrahydroquinoline.

The 1-(6-dimethylaminohexanoyl)-1,2,3,4-tetrahydroquinoline (4.0 g) was added to a mixture of lithium aluminium hydride (1.4 g) and ether (200 ml). The mixture was refluxed for 5 hours, then cooled. Water was added cautiously, and the organic solution was separated, dried and evaporated to give the title compound as an oil which is then converted to the dihydrochloride, mp 116°–119°.

EXAMPLE 2

Preparation of 4-amino-1-(1,2,3,4-tetrahydroquinolin-1-yl)butane

Sodium azide (2.2 g), 1-(4-chlorobutanoyl)-1,2,3,4-tetrahydroquinoline, prepared in a manner analogous to that set forth in Preparation 1, (4.2 g) and sodium iodide (1.5 g) were heated in dimethylformamide (25 ml) at 90° for 2 hours. The solution was poured into water and extracted with ethyl acetate. The organic solution was washed, dried and evaporated to give 1-(4-azidobutanoyl)-1,2,3,4-tetrahydroquinoline as an oil.

The 1-(4-azidobutanoyl)-1,2,3,4-tetrahydroquinoline (3.9 g) was refluxed in ether containing lithium aluminium hydride (1.8 g) for 5 hours. The solution was cooled and diluted cautiously with water. The organic phase was washed, dried and evaporated to afford the title compound as an oil, which was then converted to the dimaleate mp 79°–81°.

EXAMPLE 3

Preparation of 5-hydroxy-1-(1,2,3,4-tetrahydroquinolin-1-yl)pentane

Potassium superoxide (0.50 g) was added to a solution of 1-(5-bromopentanoyl)-1,2,3,4-tetrahydroquinoline (1.8 g) and 18-Crown-6 (0.4 g) in dimethylsulfoxide (25 ml). After 8 hours the solution was added to water and extracted with ether. The extract was washed, dried and evaporated and the residue was chromatographed on silica gel, eluting with 95:5 methylene chloride:methanol, to yield 1-(5-hydroxypentanoyl)-1,2,3,4-tetrahydroquinoline.

The 1-(5-hydroxypentanoyl)-1,2,3,4-tetrahydroquinoline (2.0 g) was refluxed for 8 hours in ether (250 ml) containing lithium aluminium hydride (1.0 g). The solution was cooled, water was added, and the ethereal solution was extracted with dilute hydrochloric acid. The extract was basified with sodium hydroxide and extracted with ether. The ethereal solution was dried and evaporated to afford the title compound as an oil.

EXAMPLE 4

Preparation of 6-methoxy-1-(1,2,3,4-tetrahydroquinolin-1-yl)hexane

Sodium methoxide (0.8 g) was added to a solution of 1-(6-bromohexanoyl)-1,2,3,4-tetrahydroquinoline (2.1 g) in methanol (50 ml). The mixture was refluxed for 8 hours, then poured into water and extracted with ether. The extract was dried and evaporated and the residue chromatographed on silica gel, eluting with 98:2 methylene chloride:methanol, so as to obtain the product 1-(6-methoxyhexanoyl)-1,2,3,4-tetrahydroquinoline.

A solution of the above 1-(6-methoxyhexanoyl)-1,2,3,4-tetrahydroquinoline (2.7 g) in ether (200 ml) containing lithium aluminium hydride (9.9 g) was refluxed for 6 hours, then cooled and diluted with water. The ethereal solution was dried and evaporated and the residue was chromatographed on silica gel, eluting with 99:1 methylene chloride:methanol, so as to obtain the title compound as an oil.

EXAMPLE 5

$N^1$-cyclohexyl-$N^2$[6-(1,2,3,4-tetrahydroquinolin-1-yl)-hexyl]urea

Cyclohexyl isocyanate (0.8 ml) was added to a solution of 6-amino-1-(1,2,3,4-tetrahydroquinolin-1-yl)hexane (3.0 g) in tetrahydrofuran (50 ml). After 1 hour, the solution was diluted with water and extracted with methylene chloride. The organic solution was dried and evaporated and the residue was fractionally crystallized to produce the title compound.

EXAMPLE 6

A. In a manner similar to that set forth in the appropriate Examples 1–5, the following compounds of the invention were prepared, and converted to their salts as set forth in Example 7.

6-amino-1-(1,2,3,4-tetrahydroquinolin-1-yl)hexane, p-toluenesulphonate, mp 72°–4°;
6-amino-1-(2,3-dihydrobenzothiazin-1-yl)hexane, hemimaleate, mp 85°–8°;
6-dimethylamino-1-(1,2,3,4-tetrahydroquinolin-1-yl)hexane, dihydrochloride, mp 116°–9°;
6-dimethylamino-1-(2,3-dihydrobenzothiazin-1-yl)hexane, p-toluenesulfonate, mp 88°–9°;
8-amino-1-(1,2,3,4-tetrahydroquinolin-1-yl)octane, p-toluenesulphonate mp, 83°–6°;
8-amino-1-(2,3-dihydrobenzothiazin-1-yl)octane, hemisuccinate, mp 122°–4°;
8-dimethylamino-1-(1,2,3,4-tetrahydroquinolin-1-yl)octane, succinate, mp 56°–8°;
8-dimethylamino-1-(2,3-dihydrobenzothiazin-1-yl)octane, p-toluenesulfonate, mp 61°–3°;
4-amino-1-(1,2,3,4-tetrahydroquinolin-1-yl)butane, dimaleate, mp 74°–81°;
4-amino-1-(2,3-dihydrobenzothiazin-1-yl), maleate, mp 144°–7°.

B. Similarly, the following compounds of the invention and their salts are prepared:
10-ethoxy-1-(6,7-dichloro-1,2,3,4-tetrahydroquinolin-1-yl)decane;
9-(N-n-propylamino)-1-(5,8-dimethoxy-2,3-dihydrobenzothiazin-1-yl)nonane;
7-(N-ethyl-N-methylamino)-1-(6-methoxybenzomorpholin-1-yl)heptane;
8-(N-2-hydroxyethyl-N-methylamino)-1-(1,2,3,4-tetrahydroquinolin-1-yl)octane;

6-(4-methylpiperazin-1-yl)-1-2,3-dihydrobenzothiazin-1-yl)hexane;

11-hydroxy-1-(6,7-diethyl-2,3-dihydrobenzoxazin-1-yl)undecane.

EXAMPLE 7

Conversion of Free Base to Salt

A twofold stoichiometric excess of 3% hydrogen chloride in methanol is added to a solution of 1.0 g. of 6-dimethylamino-1-(1,2,3,4-tetrahydroquinolin-1-yl)hexane in 20 ml methanol. Diethyl ether is added until precipitation is complete. The product is filtered, washed with ether, air dried and recrystallized to give 6-dimethylamino-1-(1,2,3,4-tetrahydroquinolin-1-yl)hexane, m.p. 142°–143.5° C.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 8

Conversion of Salt to Free Base 1.0 g of 6-dimethylamino-1-(1,2,3,4-tetrahydroquinolin-1-yl)hexane. HCl suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield 6-dimethylamino-1-(1,2,3,4-tetrahydroquinolin-1-yl)hexane as the free base.

EXAMPLE 9

Direct interchange of acid addition salts 6-dimethylamino-1-(1,2,3,4-tetrahydroquinolin-1-yl)-hexane acetate (1.0 g) is dissolved in 50 ml water containing a stoichiometric equivalent of sulfuric acid, and the solution evaporated to dryness. The product is suspended in ethanol and filtered, air dried and recrystallized from methanol/acetone to yield 6-dimethylamino-1-(1,2,3,4-tetrahydroquinolin-1-yl)-hexane bisulfate.

In Examples 10 through 15, the active ingredient is 6-dimethylamino-1-(1,2,3,4-tetrahydroquinolin-1-yl)hexane; however other compounds of Formula I and the pharmaceutically acceptable salts thereof may be substituted therein.

EXAMPLE 10

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 11

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 12

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 13

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 14

A solution preparation buffered to a pH of 7 is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water q.s. to | 100 ml |

EXAMPLE 15

A topical formulation is prepared as follows. The composition contains:

| | % wt./wt. |
| --- | --- |
| Active ingredient | 0.5 |
| Methyl paraben | 0.025 |
| Propyl paraben | 0.015 |
| Sodium lauryl sulfate | 1.0 |
| Propylene glycol | 12.0 |
| Stearyl alcohol | 25.0 |
| White petrolatum | 25.0 |
| Purified water qs. ad. | 100.0 |

The stearyl alcohol and white petrolatum are heated on a steam bath to about 75°. The other ingredients, previously dissolved in the water and warmed to 75°, are added with stirring. Stirring is continued until the mixture congeals.

We claim:

1. A method for inhibiting, preventing, or reducing inflammation which method comprises administering to a subject in need of such treatment a therapeutically effective amount of a compound of the formula:

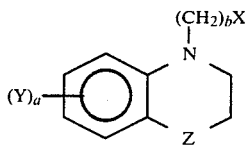

and the pharmaceutically acceptable acid addition salts thereof, wherein:

Z is S;

Y is halo, alkoxy, alkyl, or dialkylamino;

a is 0, 1 or 2;

b is an integer from 2–12 with the proviso that if b is 2 or 3, a cannot be 0, and with the further proviso that if X is OH or $NH_2$, b cannot be 2–5; and X is selected from the group consisting of: —OH, $OR^1$, —$NH_2$, —$NHR^1$, $NR_2^1$,

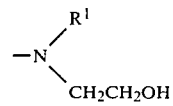

and —$NHCONHR^2$ in which each $R^1$ is independently alkyl or cycloalkyl or, in —$NR_2^1$, both $R^1$s together are alkylene or form a piperazine ring optionally substituted at the ring N by alkyl or —$CH_2CH_2OH$; and $R^2$ is alkyl, cycloalkyl, or phenyl optionally substituted with 1–3 substituents selected from the group consisting of halo, lower alkyl of 1–4 carbon atoms, lower alkoxy of 1–4 carbon atoms, hydroxy, and trifluoromethyl.

* * * * *